United States Patent [19]

Findl et al.

[11] 4,256,832

[45] Mar. 17, 1981

[54] CARCINOGEN AND MUTAGEN SCREENING METHOD AND APPARATUS

[75] Inventors: Eugene Findl, Amityville; Anthony M. Cundell, Huntington, both of N.Y.

[73] Assignee: BioResearch Inc., Farmingdale, N.Y.

[21] Appl. No.: 968,695

[22] Filed: Dec. 12, 1978

[51] Int. Cl.³ .................. C12Q 1/68; C12Q 1/29
[52] U.S. Cl. .................. 435/6; 435/29; 435/34; 435/39; 435/291; 435/807; 23/230 B; 204/195 B; 204/195 P
[58] Field of Search .......... 435/6, 29, 32, 39, 34, 435/172, 287, 291, 299, 315, 356; 204/195 B, 195 P; 23/230 B; 429/2

[56] References Cited

U.S. PATENT DOCUMENTS

| | | | |
|---|---|---|---|
| 3,765,841 | 10/1973 | Paulson et al. | 435/291 |
| 4,038,143 | 7/1977 | Juni | 435/6 |
| 4,066,510 | 1/1978 | Thilly | 435/6 |
| 4,072,574 | 2/1978 | Loeb et al. | 435/6 |

FOREIGN PATENT DOCUMENTS

2747567 4/1978 Fed. Rep. of Germany .

OTHER PUBLICATIONS

Ames et al., "Methods for Detecting Carcinogens and Mutagens with the Salmonella/Mammalian-Microsome Mutagenicity Test", *Mutation Research,* vol. 31 (1975), pp. 347-364.

Devoret, "Bacterial Tests for Potential Carcinogens", *Scientific American,* vol. 241, No. 2, (1979) pp. 40-49.

Ames et al., "An Improved Bacterial Test System for the Detection and Classification of Mutagens and Carcinogens", *Proc. Nat. Acad. Sci.,* vol. 70, No. 3, (1973), pp. 782-786.

McCann et al., "Detection of Carcinogens as Mutagens in the Salmonella/Microsome Test: Assay of 300 Chemicals", *Proc. Nat. Acad. Sci.,* vol. 72, No. 12 (1975), pp. 5135-5139.

McCann et al., "Detection of Carcinogens as Mutagens in the Microsome Test: Assay of 300 Chemicals Discussion", *Proc. Nat. Acad. Sci.,* vol. 73, No. 3 (1976), pp. 950-954.

McCann et al., "A Simple Method for Detecting Environmental Carginogens as Mutagens", *Annals N.Y. Acad. Sci.,* vol. 271, pp. 5-13.

*Primary Examiner*—Thomas G. Wiseman
*Attorney, Agent, or Firm*—Larson, Taylor and Hinds

[57] ABSTRACT

A method of screening a material for potential carcinogenic or mutagenic activity. A mutant stain of eucaryotic or prokaryotic test organism is provided which is capable of reverting to a normal form in the presence of a carcinogen or mutagen. A growth media is provided in which the test organism is capable of growth in one only of its mutant forms. For example, the test organism may be a bacteria which in its mutant form is incapable of substantial growth in the absence of an essential nutrient and, in its natural form, is capable of rapid growth in the absence of that nutrient. The test organism and growth media are combined with oxygen and a material to be screened. Oxygen consumption is then detected to determine if the mutant strain has reverted to its normal form. Reversion is indicated if a change in oxygen consumption occurs when the material being screened is present.

15 Claims, 4 Drawing Figures

CARCINOGEN AND MUTAGEN SCREENING METHOD AND APPARATUS

BACKGROUND OF THE INVENTION

In recent years, national and international attention has become focused on the problem of the release into the environment of chemical reagents that are potential health hazards. The problem is complicated by the socio-economic aspects of production and use of these chemicals and by our limited knowledge of the long term effects of such reagents, with regard to their carcinogenicity and mutagenicity. The public obviously cannot afford to wait five to twenty five years after the introduction of a new reagent to see if it is a health hazard. Methods for evaluation or screening of potentially hazardous materials are therefore needed that provide an indication of the degree of hazard in relatively short time periods.

There have been a number of approaches to evaluation and/or screening of chemicals to evaluate their hazard potential. Since the problem is one of the effect of chemicals on biological entities, the approaches have centered on bioassay procedures. The range of biota chosen for controlled exposure to potentially hazardous chemicals has been enormous. On one end of the spectrum are single cells such as bacteria yeast and mammalian cells. At the other end are multifunctional organisms, such as plants and animals. In general, the tendency has been towards screening with less biologically complex entities, followed by more definitive confirmation testing with complex biota of those chemicals found hazardous in the screening effort.

Among the generally accepted screening procedures for carcinogens and mutagens is the so-called Ames test developed by Dr. Bruce N. Ames and his associates. The Ames test is based upon the assumption that carcinogens will cause the genetic reversion of certain mutant strains of bacteria such as *Salmonella typhimurium*. In other words, the mutant strains revert to their normal or "wild" form in the presence of carcinogens and mutagens. Since the majority of mutagens or their metabolic products are also carcinogens, the Ames test is also used to screen this class of chemicals. Extensive testing with a wide variety of potential carcinogens has indicated the general validity of the basic assumption that carcinogens cause bacterial reversion.

Basically, the mutant *Salmonella typhimurium* strains are selected because they lack the ability to produce histidine, an essential amino acid. These mutants are unable to multiply unless this essential nutrient is present in their growth media. In the presence of carcinogens and mutagens, the mutated strains revert to their "wild" form. Since the "wild" forms can manufacture histidine from other materials, it need not be present in the growth media in order for the reverted strains to multiply. Thus, by culturing mutant strains of *Salmonella typhimurium* in a media that does not contain histidine or contains a minimal amount of histidine, but does contain a suspected chemical, one can evaluate the carcinogenicity or mutagenicity by determining the growth charactristics. It is not, however, a go, no-go situation, since there is a certain portion of the mutant bacteria that reverts spontaneously, without any experimental stimulus. This "natural" reversion rate phenomena represents a "noise level" that limits the overall sensitivity of the test. It is not a critical factor with properly chosen bacterial strains, i.e. those with low spontaneous reversion rates.

As with most bacterial tests, plate counting techniques are used to determine the number of revertant bacteria. For the Ames test, plate counting requires a 48 hour growth period, plus time to count both the test plates and control plates used to monitor spontaneous reversion. The Ames test is discussed more fully in an article by Ames et al appearing in *Mutation Research*, Volume 31 (1975) pages 347–364.

It is an object of the present invention to provide a rapid screening of potential carcinogens or mutagens. It is a further object to reduce the effort required for such screening. It is still a further object of the invention to provide suitable apparatus for carrying out this method.

BRIEF SUMMARY OF THE INVENTION

The foregoing and other objects which will be apparent to those having ordinary skill in the art are achieved in accordance with the present invention by a method which includes the following steps: (a) providing a mutant strain of eucaryotic or prokaryotic test organism capable of reverting to a normal form in the presence of a carcinogen or mutagen; (b) providing a growth media in which the test organism is capable of rapid growth in one only of its mutant or normal forms; (c) combining the mutant strain of test organism and the growth media; (d) contacting the combined test organism and growth media with a material to be screened in the presence of oxygen; (e) detecting the consumption of oxygen resulting from step (d) to determine if the mutant strain of test organism has reverted to its normal form to thereby determine if the material to be screened is potentially carcinogenic or mutagenic; and by providing apparatus for carrying out the method, the apparatus including: oxygen electrode means for generating an electrical signal proportional to the amount of oxygen detected; a test organism-containing material adjacent the oxygen electrode, the material comprising a mutant strain of test organism capable of reverting to a normal form in the presence of a carcinogen or mutagen, and a growth media in which the test organism is capable of rapid growth in one only of its mutant and normal forms; means for contacting the test organism-containing material with an oxygen-containing gas; and means for detecting the consumption of oxygen by the test organism.

DESCRIPTION OF PREFERRED EMBODIMENTS

For a more detailed understanding of the invention, reference is made to the following description of various embodiments thereof and to the accompanying drawings in which.

Figure 1:
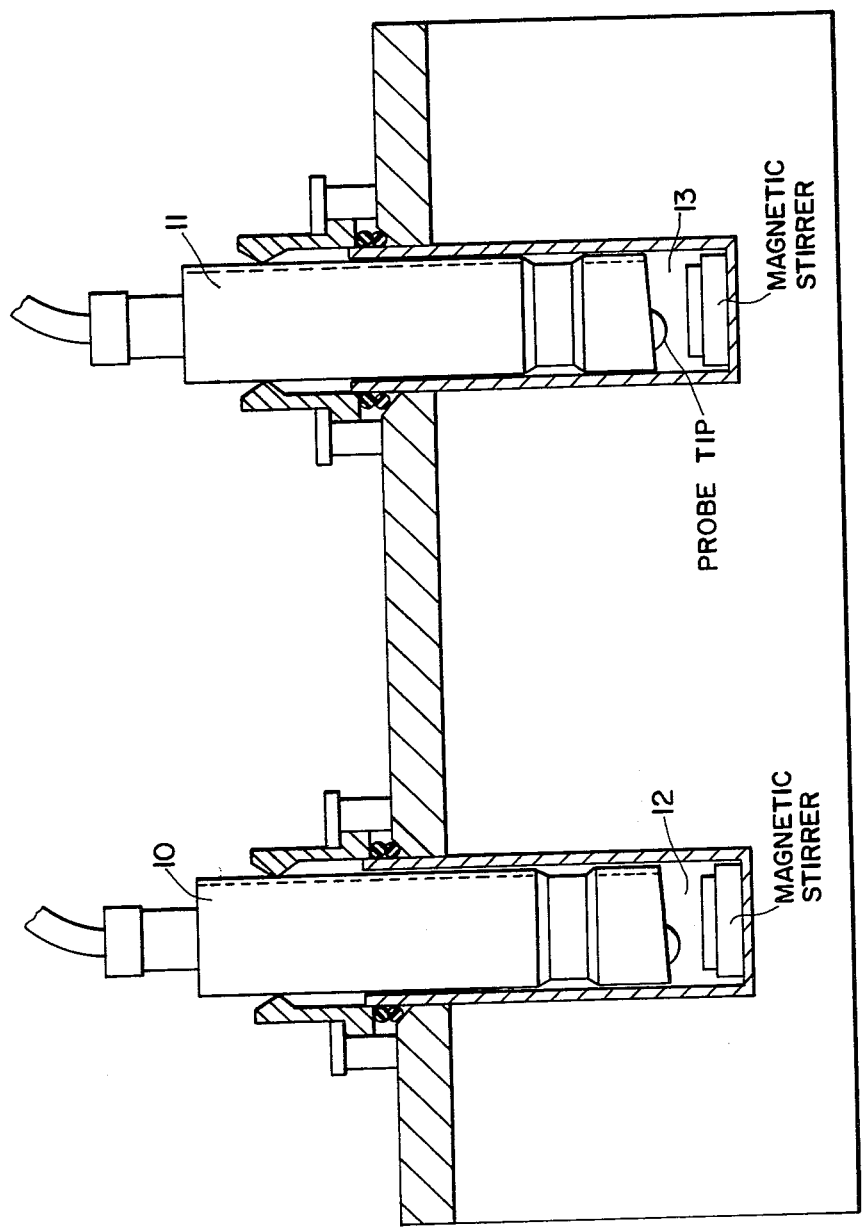
FIG. 1 is a diagrammatic side elevation sectional view of apparatus in accordance with the invention.

In the device illustrated in FIG. 1, two conventional oxygen electrodes, 10, 11, of the Clark type are employed. Electrode 10, designated the control electrode, measures the respiration rate ($O_2$ uptake) of a fixed volume 12 and concentration of Ames test bacteria in a media that contains at most a minimal amount of histidine and does not contain the chemical to be evaluated for carcinogenicity and/or mutagenicity. Electrode 11, designated the test electrode, measures the respiration rate (O₂ uptake) of the same fixed volume 13 and concentration of Ames test bacteria and media as the control electrode. In the second case, the media also contains the chemical to be evaluated. If the chemical is a carcinogen or mutagen, the O₂ uptake of test electrode 11 will increase at a faster rate than that of the control. This occurs because the reversion rate, and thus the growth rate and O₂ consumption rate will be higher in the test electrode 11 than in the control electrode 10. Conversely, if the chemical is not a carcinogen or a mutagen, the O₂ uptake rates will be similar. Thus, by measuring the difference in O₂ uptake rates between a control and a test electrode, the potential carcinogenicity and/or mutagenicity of a chemical can be evaluated. The difference measurement can be made by any of the many electronic techniques used for such measurements or by simple manual subtraction.

Since O₂ uptake does not require the growth of colonies of bacteria needed for visual counting of plates, several hours of growth should be sufficient for O₂ uptake difference measurements to be made. Thus, test time can be reduced from 48 hours to, for example 2 hours (neglecting sample preparation time, which would be similar for both the conventional technique and the present technique). Further, plate counting time and cost is eliminated, because differences in reversions are measured directly by the difference output of the electrodes. In principle, the greater the current difference, the greater the carcinogenic/mutagenic potential of the chemical, assuming identical test conditions for each chemical.

Various test organisms can be used, both eucaryotic and prokaryotic. The test organism is one which, in the presence of a known carcinogen or mutagen will revert from its mutant form to its wild form and which is capable of growth, in a selected medium, in only one of its two forms. The media is one which will support substantial or rapid growth of the test organism in one only of its two forms. In one embodiment, the media contains none or a minimal amount of a nutrient which is essential to growth of the test organism in one of its forms but not the other. For example, histidine is essential to the growth of certain mutant forms of *Salmonella typhimurium* whereas, in its normal or wild form, it has the ability to produce histidine. Accordingly, while the presence of histidine is required for substantial or rapid growth of the mutant strain, it is not required for growth of the bacteria in its normal form. In a similar system, a test organism is selected that, in its normal form, will not grow in the absence of an essential nutrient but will grow in the absence of that nutrient when in its nutrient form. An example is mammalian cells such as L5i78y Murine leukemia cells which, in their normal form require the essential nutrient asparagine but which, in their mutant form will grow in the absence of that nutrient. In another embodiment, the growth media contains a material which is a biocide to the one form of the test organism but not the other. For example, cavanine sulfate is toxic to the normal form of the yeast *Saccharomyces cerevsiae* but not to its mutant form. Accordingly, if reversion to normal form is caused by a suspected carcinogen, oxygen consumption will decrease because of the toxic effect of the biocide on the normal form of the yeast cells. Similarly, L-azetidine carboxylic acid is toxic to the normal form of *S. typhimurium* TA 1530 but is not toxic to its mutant form. Accordingly, potential carcinogenicity in this system is indicated by decreasing oxygen consumption caused by the biocidal effect of the acid on the normal form of the bacteria.

In general, the following criteria apply to the selection of preferred test organisms/growth media systems:
1. a low spontaneous mutation rate (low "noise" level);
2. high induced mutation rate;
3. low endogenous respiration;
4. rapid cell growth and concomittant respiration of mutants;
5. sensitivity to both frame shift and base pair mutations.

When testing the effects of unknown substances and one of the criteria involves the measurement of O₂ uptake, there is always the possibility that the unknown substances is an uncoupler of oxidative phosphorylation. If this is the case, a very rapid increase in oxygen uptake will be registered. This oxygen uptake, however, is independent of "real" respiration and no ATP (adenosine triphosphate) will be produced. One of the best known uncouplers of oxidative phosphorylation is dinitrophenol. Naturally occurring substances, such as the thyroid hormones thyroxine and triiodothyronine, stimulate respiration and ATP production in low concentrations ($10^{-9}$ M) and uncouple at higher concentrations. Thus, any substance that produces an increase in oxygen uptake, independent of increased numbers of organisms, should be tested for uncoupling activity.

Figure 2:
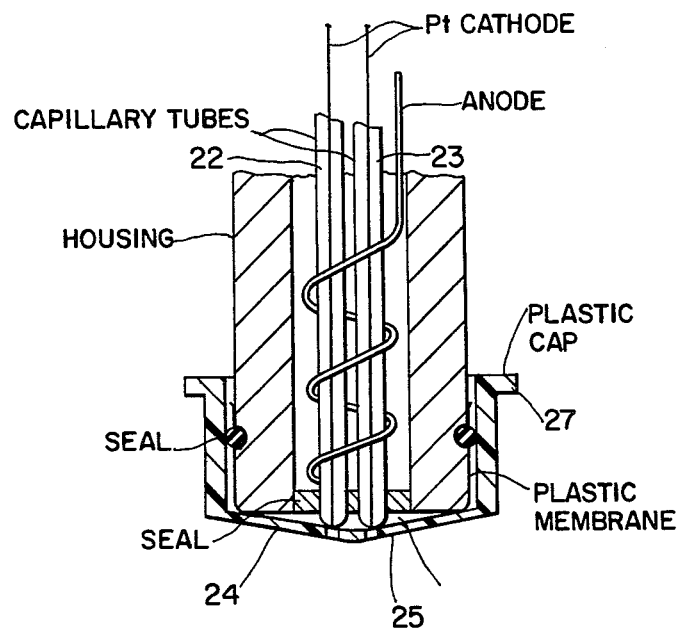
FIG. 2 is a diagrammatic side elevation view of an alternative apparatus.
Figure 3:
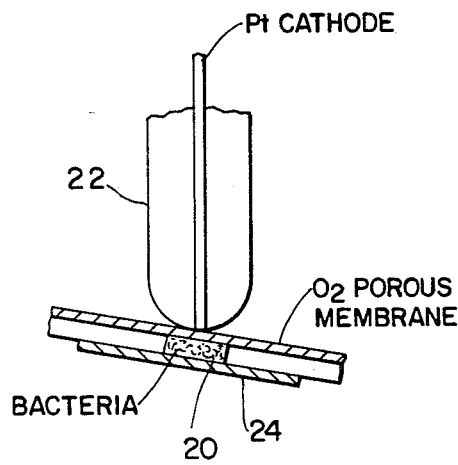
FIGS. 3 and 4 are enlarged diagrammatic side elevation views of portions of the apparatus of FIG. 2.
Figure 4:
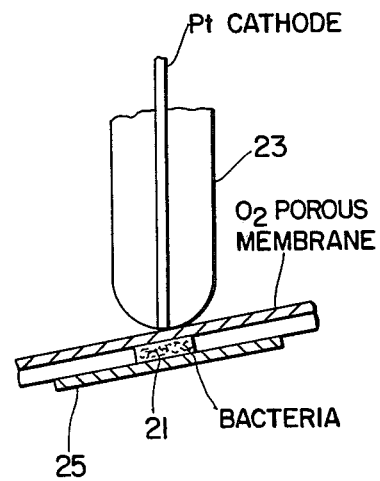

It will be apparent to those of ordinary skill in the art that there are a number of variatons of the invention that can be employed. As indicated above, various test organisms can be employed. One can, of course, use one electrode and measure both test and control samples separately. A more refined approach would be to utilize the Updike and Hicks type electrode shown in FIG. 2. This electrode is more compact, requires less bacteria, and should be more sensitive thus, resulting in an even faster test. Oxygen electrodes and their operation are well known. A succinct description thereof will be found in an article entitled "Electrodes for the Measurement of Oxygen and Carbon Dioxide Tensions" by Smith et al, appearing at pages 731-735 of the *British Journal of Anaesthesia* (1969) Volume 41.

Several strains of *Salmonella typhimurium*, such as TA100, TA98, TA1535 and TA1537 are placed in small containment volumes 20, 21 (approximately 1 ml) at the tip of oxygen electrodes 22, 23. Containment volume 20 is provided with an overlying membrane 24 which is permeable to the reagent in question and to oxygen. Containment volume 21 is similarly covered with an overlying membrane 25 which is permeable to oxygen but not to the chemical agent. An atmosphere containing oxygen and the chemical to be screened is provided adjacent membranes 24 and 25 such as by inserting the entire electrode structure into a suitable aperture of a vessel (not shown) containing the atmosphere, using flange 27 of the electrode structure to secure the electrode to the containment vessel. Oxygen uptake of the two electrodes is then detected as described above to determine if the reagent in question is a potential carcinogen or mutagen.

The same approach can be taken using two separate oxygen electrodes having membranes that will permit the chemicals in question to diffuse into bacteria-containing chamber. In use, one of the electrodes is immersed into a vessel containing the suspected chemical while the second electrode would be immersed in a vessel having the same contents but absent the suspected chemical. The difference in the oxygen uptake, as indicated by the difference in the electrical output of the electrodes, is again a measure of potential carcinogenic or mutagenic activity of the chemical in question.

It is also possible to screen chemicals using a single oxygen electrode. In this case, results are compared with previously obtained control results such as in the form of a standard curve of oxygen uptake as a function of time obtained using no suspected chemical.

EXAMPLE

The test organism, *S. typhimurium* TA 1535 is grown overnight, washed three times in phosphate buffer and resuspended to give OD of 0.8 ($>10^8$ per ml). Ten ml. of minimal glucose medium is added to sterile flasks. Histidine is added to the flasks to give: (a) flask #1—full histidine; (b) flask #2—no histidine; and (c) flask #3 and #4—minimal histidine. The known mutagen 9-amine acridine is added to flask #3 at a level of 10 Mg/ml and to flask #4 at a level of 5 Mg/ml. One ml of innoculum is added to each flask and the flasks are incubated at 35° C. in a shaking incubator. At zero, four, and 32 hours, 1 ml of culture is added to 2 ml of aerated minimal glucose media in the test chamber of an oxygen electrode and the rate of oxygen uptake is measured. The results are tabulated in the following table:

| Flask No. | Histidine Level | Mutagen Level Mg/ml | $O_2$ Uptake $\mu$moles/min. | | |
|---|---|---|---|---|---|
| | | | 0 hrs. | 4 hrs. | 32 hrs. |
| 1 | Full | 0 | 0.02814 | 0.06678 | 0.39708 |
| 2 | Zero | 0 | — | 0.01873 | 0.1403 |
| 3 | Minimal | 10 | — | 0.04772 | 0.28723 |
| 4 | Minimal | 5 | — | 0.04772 | 0.16736 |

It will be readily apparent that the oxygen uptake for flasks 3 and 4 is dependent upon the level of the added known mutagen. Thus, the test provides a method of detecting the potential carcinogenicity or mutagenicity of a suspected substance.

What is claimed is:

1. A method of screening a material for potential carcinogenic or mutagenic activity comprising:
   (a) providing a mutant strain of eucaryotic or prokaryotic test organism capable of reverting to a normal form in the presence of a carcinogen or mutagen;
   (b) providing a growth media in which the test organism is capable of rapid growth in one only of its mutant or normal forms;
   (c) combining said mutant strain of test organism and said growth media;
   (d) contacting the combined test organism and growth media with a material to be screened in the presence of oxygen;
   (e) detecting the consumption of oxygen resulting from step (d) to determine if said mutant strain of test organism has reverted to its normal form to thereby determine if said material to be screened is potentially carcinogenic or mutagenic.

2. A method according to claim 1 wherein said detecting step (e) comprises comparing said consumption of oxygen with a previously determined standard of oxygen consumption.

3. A method according to claim 1 wherein said step (e) of detecting oxygen consumption comprises positioning an oxygen electrode adjacent the combined mutant strain of test organism and growth media and analyzing an electrical output signal of said electrode.

4. A method according to claim 1 comprising providing first and second portions of the combined mutant strain of test organism and said growth media, contacting said first portion thereof with a material to be screened and oxygen according to step (d), contacting said second portion thereof with oxygen in the abscence of said material to be screened, and comparing consumption of oxygen resulting from the contacting steps to determine if said mutant strain of test organism has reverted to its normal form to thereby determine if said material to be screened is potentially carcinogenic or mutagenic.

5. A method according to claim 4 wherein comparison of oxygen consumption is effected by positioning a first oxygen electrode adjacent said first portion of combined test organism and growth media, positioning a second oxygen electrode adjacent said second portion of combined test organism and growth media, and comparing electrical output signals of the first and second oxygen electrodes.

6. A method according to claim 1 wherein said test organism, in its mutant form is substantially incapable of growth in the absence of an essential nutrient and, in its natural form, is capable of growth in the absence of said nutrient, wherein said media is substantially free of said essential nutrient, and wherein reversion of the test organism to its natural form is indicated by increased consumption of oxygen resulting from step (d).

7. A method according to claim 1 wherein said test organism comprises a mutant strain of the bacteria *Salmonella typhimurium*.

8. A method according to claim 7 wherein said essential nutrient is histidine.

9. A method according to claim 1 wherein said test organism, in its natural form, is substantially incapable of growth in the absence of an essential nutrient and, in its mutant form is capable of growth in the absence of said essential nutrient, wherein said media is substantially free of said essential nutrient, and wherein reversion of the test organism to its natural form is indicated by decreased consumption of oxygen resulting from step (d).

10. A method according to claim 9 wherein said test organism comprises a mutant strain of the mammalian L5i78y Murine leukemia cell.

11. A method according to claim 10 wherein said essential nutrient comprises asparagine.

12. A method according to claim 1 wherein said test organism, in its natural form, is susceptible to attack of a biocide and, in its mutant form is substantially non-susceptible to attack of said biocide, wherein said media contains said biocide, and wherein reversion of the test organism to its natural form is indicated by decreased consumption of oxen resulting from step (d).

13. A method according to claim 12 wherein said test organism comprises a mutant strain of the yeast *Saccharomyces cerevisiae* and wherein said biocide comprises canavanine sulphate.

14. A method according to claim 12 wherein said test organism comprises a mutant strain of *S. typhimurium* TA1530 and wherein said biocide comprises L-azetidine carboxylic acid.

15. A method according to claim 1 wherein said material to be screened is present in said growth media.

* * * * *